(12) United States Patent
Moore et al.

(10) Patent No.: US 10,596,402 B2
(45) Date of Patent: Mar. 24, 2020

(54) OZONE CLEANING SYSTEM

(71) Applicant: Oshkosh Corporation, Oshkosh, WI (US)

(72) Inventors: Michael R. Moore, New London, WI (US); Matthew M. McLeish, Oshkosh, WI (US); John Schultz, Appleton, WI (US)

(73) Assignee: Oshkosh Corporation, Oshkosh, WI (US)

( * ) Notice: Subject to any disclaimer, the term of this patent is extended or adjusted under 35 U.S.C. 154(b) by 0 days.

(21) Appl. No.: 16/373,123

(22) Filed: Apr. 2, 2019

(65) Prior Publication Data

US 2019/0224516 A1 Jul. 25, 2019

Related U.S. Application Data

(63) Continuation of application No. 16/213,174, filed on Dec. 7, 2018.
(Continued)

(51) Int. Cl.
*A61L 2/20* (2006.01)
*A62D 3/38* (2007.01)
(Continued)

(52) U.S. Cl.
CPC .............. *A62D 3/38* (2013.01); *A61L 2/202* (2013.01); *A62B 29/00* (2013.01); *B01D 53/8687* (2013.01); *B01J 12/00* (2013.01); *B01J 21/063* (2013.01); *B01J 35/004* (2013.01); *B60S 1/64* (2013.01); *B65F 3/00* (2013.01); *C01B 13/10* (2013.01); *A61L 2202/16* (2013.01);
(Continued)

(58) Field of Classification Search
CPC ...... A62D 29/00; A62D 3/38; B01D 53/8687; B01J 12/00; B01J 21/063; A61L 2/20
See application file for complete search history.

(56) References Cited

U.S. PATENT DOCUMENTS 3,521,459 A 7/1970 Rath
5,015,442 A 5/1991 Hirai
(Continued)

FOREIGN PATENT DOCUMENTS

CA 2782363 7/2011
DE 100 60 478 6/2002
(Continued)

OTHER PUBLICATIONS

Partial Search Report Received for Application No. PCT/US2018/064459, Oshkosh Corporation, dated Apr. 3, 2019, 20 pages.
(Continued)

*Primary Examiner* — Sean E Conley
(74) *Attorney, Agent, or Firm* — Foley & Lardner LLP

(57) ABSTRACT

An ozone cleaning system includes a first chamber, a second chamber coupled to the first chamber, and a utility assembly disposed within the second chamber. The utility assembly includes an ozone generator configured to provide ozone to the first chamber, a humidifying unit configured to provide water vapor to the first chamber, and a blower configured to at least one of (i) reduce air pressure within the first chamber or (ii) draw the ozone from the first chamber following a decontamination process.

12 Claims, 10 Drawing Sheets

Related U.S. Application Data

(60) Provisional application No. 62/662,010, filed on Apr. 24, 2018, provisional application No. 62/662,017, filed on Apr. 24, 2018, provisional application No. 62/596,464, filed on Dec. 8, 2017.

(51) Int. Cl.

| | | |
|---|---|---|
| *C01B 13/10* | (2006.01) | |
| *B01D 53/86* | (2006.01) | |
| *B01J 21/06* | (2006.01) | |
| *B01J 35/00* | (2006.01) | |
| *B01J 12/00* | (2006.01) | |
| *B60S 1/64* | (2006.01) | |
| *B65F 3/00* | (2006.01) | |
| *A62B 29/00* | (2006.01) | |
| *A62D 101/08* | (2007.01) | |

(52) U.S. Cl.
CPC ....... *A61L 2202/26* (2013.01); *A62D 2101/08* (2013.01); *B01D 2255/20707* (2013.01); *B01D 2255/802* (2013.01); *B01D 2258/06* (2013.01)

(56) References Cited

U.S. PATENT DOCUMENTS

| | | |
|---|---|---|
| 5,137,697 A | 8/1992 | Lathan et al. |
| 5,221,520 A | 6/1993 | Cornwell |
| 5,266,275 A | 11/1993 | Faddis |
| 5,344,622 A | 9/1994 | Faddis et al. |
| 5,681,533 A | 10/1997 | Hiromi |
| 5,833,740 A | 11/1998 | Brais |
| 5,961,919 A | 10/1999 | Tachibana et al. |
| 5,968,214 A | 10/1999 | Nagata et al. |
| 6,066,294 A | 5/2000 | Lin et al. |
| 6,224,828 B1 | 5/2001 | Lin et al. |
| 6,447,731 B1 | 9/2002 | Sun et al. |
| 6,508,982 B1 | 1/2003 | Shoji |
| 6,528,015 B1 | 3/2003 | Lin et al. |
| 6,589,486 B1 | 7/2003 | Spanton |
| 6,620,379 B1 | 9/2003 | Piuk et al. |
| 6,939,336 B2 | 9/2005 | Silfver |
| 6,977,061 B2 | 12/2005 | Lin et al. |
| 7,234,534 B2 | 6/2007 | Froland et al. |
| 7,285,254 B2 | 10/2007 | Lin et al. |
| 7,294,305 B2 | 11/2007 | Lin et al. |
| 7,326,387 B2 | 2/2008 | Arts et al. |
| 7,331,586 B2 | 2/2008 | Trinkner et al. |
| 7,407,633 B2 | 8/2008 | Potember et al. |
| 7,452,410 B2 | 11/2008 | Bergeron et al. |
| 7,468,159 B2 | 12/2008 | Lin et al. |
| 7,504,066 B2 | 3/2009 | Perlov et al. |
| 7,527,603 B2 | 5/2009 | An |
| 7,588,720 B2 | 9/2009 | Turcot et al. |
| 7,615,030 B2 | 11/2009 | Murphy et al. |
| 7,784,554 B2 | 8/2010 | Grady et al. |
| 7,803,316 B2 | 9/2010 | Lin et al. |
| 8,114,358 B2 | 2/2012 | Benedek et al. |
| 8,211,374 B2 | 7/2012 | Hallam |
| 8,277,740 B2 | 10/2012 | Pattee |
| 8,318,084 B2 | 11/2012 | Johnson et al. |
| 8,357,331 B2 | 1/2013 | McVey et al. |
| 8,376,719 B2 | 2/2013 | Grady et al. |
| 8,388,900 B2 | 3/2013 | Benedek et al. |
| 8,529,831 B1 | 9/2013 | Ho et al. |
| 8,529,832 B2 | 9/2013 | Lee |
| 8,668,883 B2 | 3/2014 | Garner |
| 8,739,892 B2 | 6/2014 | Moore et al. |
| 8,777,889 B2 | 7/2014 | Joshi et al. |
| 8,875,547 B2 | 11/2014 | Suzuki et al. |
| 8,986,520 B2 | 3/2015 | Joshi et al. |
| 9,327,150 B2 | 5/2016 | Moore et al. |
| 9,504,863 B2 | 11/2016 | Moore |
| 9,539,076 B2 | 1/2017 | Almutairi |
| 9,597,536 B1 | 3/2017 | Moore |
| 9,814,915 B2 | 11/2017 | Moore |
| 2002/0074290 A1 | 6/2002 | Jensen |
| 2003/0113246 A1 | 6/2003 | Saitou et al. |
| 2004/0022673 A1 | 2/2004 | Protic |
| 2005/0097870 A1 | 5/2005 | Moshenrose |
| 2005/0163678 A1 | 7/2005 | Clawson et al. |
| 2006/0104858 A1 | 5/2006 | Potember et al. |
| 2007/0039626 A1 | 2/2007 | Schulz |
| 2007/0181000 A1 | 8/2007 | Wilson et al. |
| 2008/0170971 A1* | 7/2008 | Bergeron ............... A61L 9/205 422/171 |
| 2009/0162255 A1* | 6/2009 | Chan .................... F24F 3/1603 422/169 |
| 2009/0252654 A1 | 10/2009 | Hsu et al. |
| 2009/0311138 A1* | 12/2009 | Klaptchuk ............. A61L 2/202 422/30 |
| 2010/0003164 A1 | 1/2010 | Bourne et al. |
| 2010/0112677 A1 | 5/2010 | Onishi et al. |
| 2010/0196198 A1 | 8/2010 | Legube |
| 2011/0033346 A1 | 2/2011 | Bohlen et al. |
| 2011/0076192 A1 | 3/2011 | Robitaille et al. |
| 2011/0091354 A1 | 4/2011 | Schwartz et al. |
| 2012/0003126 A1 | 1/2012 | Engelhard |
| 2012/0189490 A1 | 7/2012 | Van Den Bossche et al. |
| 2013/0047857 A1 | 2/2013 | Bohlen |
| 2013/0287626 A1 | 10/2013 | Benedek et al. |
| 2016/0265796 A1 | 9/2016 | Carbone et al. |
| 2017/0246333 A1 | 8/2017 | Carbone et al. |
| 2018/0036446 A1 | 2/2018 | Rice et al. |
| 2018/0064973 A1 | 3/2018 | Moore |
| 2018/0264157 A1 | 9/2018 | Benedek et al. |
| 2018/0264160 A1 | 9/2018 | Benedek et al. |
| 2018/0361009 A1 | 12/2018 | Kim et al. |
| 2019/0030195 A1* | 1/2019 | Hatti ....................... B64F 5/30 |
| 2019/0240370 A1 | 8/2019 | Benedek et al. |
| 2019/0240371 A1 | 8/2019 | Benedek et al. |

FOREIGN PATENT DOCUMENTS

| | | |
|---|---|---|
| DE | 20 2017 007 059 | 6/2019 |
| EP | 2 651 536 A1 | 10/2013 |
| JP | 02-174987 | 7/1990 |
| JP | 02-174988 | 7/1990 |
| JP | 2000-202493 A | 7/2000 |
| JP | 2000-202793 | 7/2000 |
| JP | 2001-212586 | 8/2001 |
| JP | 2001-219181 | 8/2001 |
| JP | 2004-019957 | 1/2004 |
| WO | WO-2008/082452 A1 | 7/2008 |
| WO | WO-2011/038487 A1 | 4/2011 |
| WO | WO-2013/110782 A1 | 8/2013 |
| WO | WO-2018/167528 A1 | 9/2018 |
| WO | WO-2019/147501 | 8/2019 |
| WO | WO-2019/152996 | 8/2019 |

OTHER PUBLICATIONS

International Search Report and Written Opinion on PCT/US2018/064459, dated May 24, 2019, 24 pages.
Non-Final Office Action on U.S. Appl. No. 16/373,069, dated May 31, 2019, 21 pages.
Scent Crusher: Ozone Hunter's Closet, obtained from website: http://scentcrusher.com/hunters-closet/, 3 pps.
Scent Crusher: Ozone Go, obtained from website: https://scentcrusher.com/ozone-go/, 8 pps.

\* cited by examiner

OZONE CLEANING SYSTEM

CROSS-REFERENCE TO RELATED PATENT APPLICATIONS

The present application is a continuation of U.S. patent application Ser. No. 16/213,174, filed Dec. 7, 2018, which claims the benefit of U.S. Provisional Patent Application No. 62/596,464, filed Dec. 8, 2017, U.S. Provisional Patent Application No. 62/662,010, filed Apr. 24, 2018, and U.S. Provisional Patent Application No. 62/662,017, filed Apr. 24, 2018, all of which are incorporated herein by reference in their entireties.

BACKGROUND

Fire fighters are at a higher risk of health ailments (e.g., cancer) than the general public. This has been attributed to carcinogens released from burning materials at the scene of a fire. Studies have shown that carcinogens on firefighting gear can gas off up to nine hours after exposure, and thus increase the risk to fire fighters that use the exposed gear.

SUMMARY

One embodiment relates to an ozone cleaning system. The ozone cleaning system includes a first chamber, a second chamber coupled to the first chamber, and a utility assembly disposed within the second chamber. The utility assembly includes an ozone generator configured to provide ozone to the first chamber, a humidifying unit configured to provide water vapor to the first chamber, and a blower configured to at least one of (i) reduce air pressure within the first chamber or (ii) draw the ozone from the first chamber following a decontamination process.

Another embodiment relates to a vehicle. The vehicle includes a chassis, a front cab coupled to the chassis, and an ozone cleaning system. The front cab defines an interior. The ozone cleaning system is positioned within the interior of the front cab. The ozone cleaning system is configured to decontaminate at least one of (i) the interior of the front cab or (ii) at least one of gear or equipment disposed within a housing of the ozone cleaning system by treating organic carcinogens.

Still another embodiment relates to a vehicle. The vehicle includes a chassis, a front cab coupled to the chassis, a rear assembly coupled to the chassis and positioned rearward of the front cab, and an ozone cleaning system. The rear assembly includes a selectively accessible compartment. The ozone cleaning system is positioned within the selectively accessible compartment. The ozone cleaning system is configured to decontaminate at least one of gear or equipment disposed within the selectively accessible compartment of the rear assembly by treating organic carcinogens The invention is capable of other embodiments and of being carried out in various ways. Alternative exemplary embodiments relate to other features and combinations of features as may be recited herein.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Figure 1:
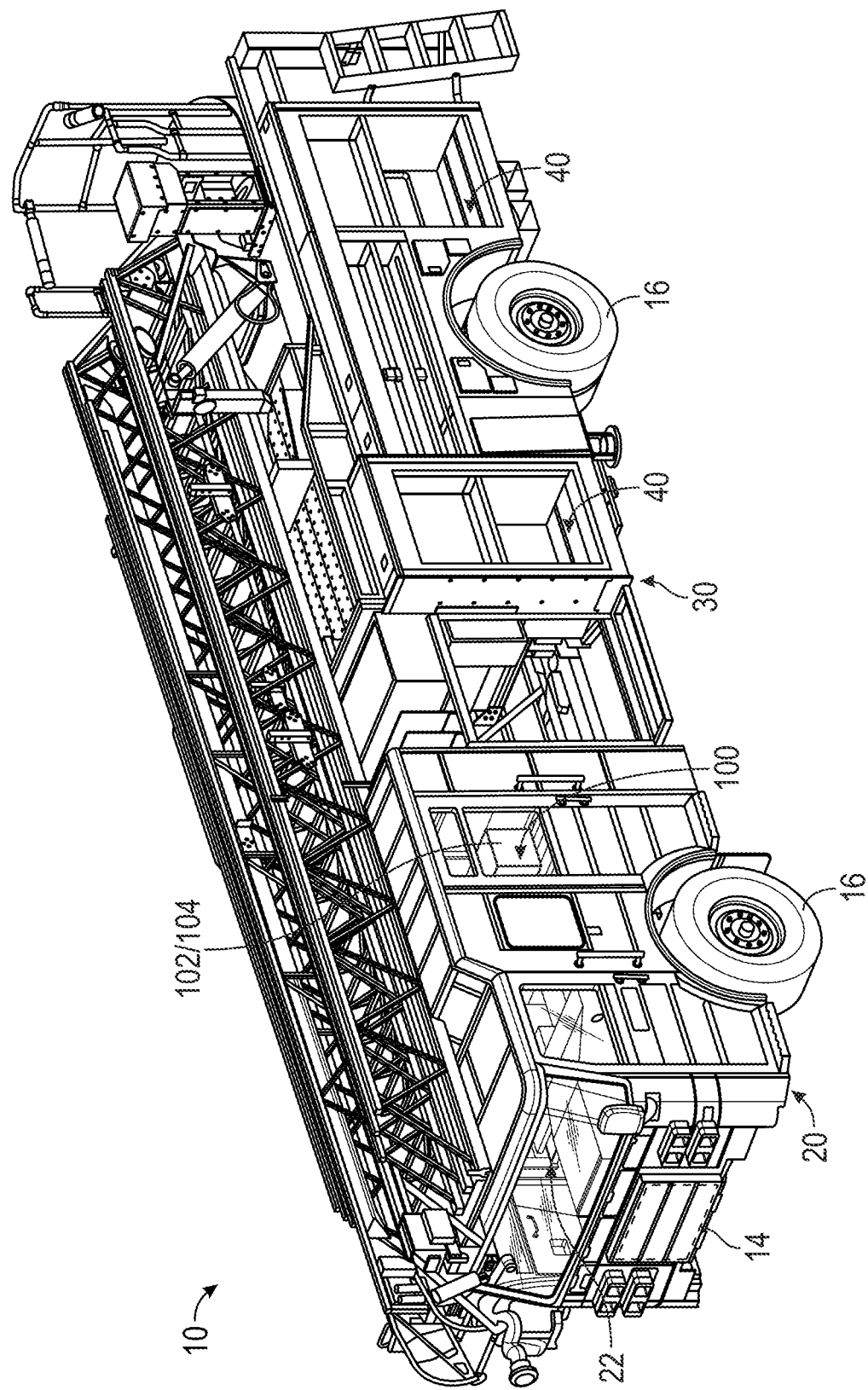
FIG. 1 is a perspective view of a fire fighting vehicle, according to an exemplary embodiment.

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

According to an exemplary embodiment, an ozone cleaning system is configured to facilitate decontaminating at least one of a space (e.g., an interior of a vehicle, etc.), gear, and equipment. In one embodiment, the ozone cleaning system is a standalone unit having a housing that may be positioned inside of a cab of a vehicle, inside of a compartment of a vehicle, inside of a building, etc. In another embodiment, the ozone cleaning system is integrated into a cab of a vehicle and/or a compartment of the vehicle. Advantageously, the ozone cleaning system may facilitate treating gear and equipment at the scene of a fire, on the fire truck, or at the station quickly, therefore eliminating the need for multiple sets of equipment for each fire fighter. Additionally or alternatively, the ozone cleaning system may advantageously facilitate treating the interior of cabs of fire trucks (or other types of vehicles) where carcinogens and/or other harmful contaminants can build up over time.

First-responders are often exposed to hazardous situations during the course of their duties. One of the most dangerous situations arises when personnel are exposed to hazardous chemicals. Trace amounts of these chemicals may coat the surface of clothing and protective gear of the first-responders, and given their toxicity, can be harmful. For example, one of the simplest molecules is a chemical called benzene. Benzene is produced from crude oil and is an important component of gasoline and other petroleum products. However, benzene is known to cause cancer. There is no level of benzene that is completely safe. Exposure can cause multiple forms of leukemia, as well as heart problems and bone marrow disease. Benzene also targets the lungs, liver, kidneys, and can even cause DNA damage. Dealing with trace contaminants of benzene (i.e., levels too low to be smelled or detected by the eye, yet still dangerously high in terms of potential health effects) is a challenge. Benzene is not even the most dangerous pollutant. Compounds such as benzopyrene, butadiene, formaldehyde, dibenzanthracene, trichloroethylene, tetrachloroethylene, and polychlorinated biphenyls are all present in the environment either from their past use in industry (e.g., in cleaning products, lubricants, etc.) or as decomposition products from other compounds that are used.

According to an exemplary embodiment, the ozone cleaning system of the present disclosure is configured to implement a decontamination process that uses ozone, moist/humidified air, and/or ultraviolet light to break down such dangerous compounds into harmless carbon dioxide, water, and/or chloride salts. Ozone is a pale blue gas that is generated naturally in the upper atmosphere, but can also be generated using specifically designed devices. There really is no practical way to store Ozone such that it must be generated as needed (i.e., because of its high reactivity). Regular oxygen that we breathe consists of two oxygen atoms bound together, and is represented as $O_2$. Ozone is related to oxygen, but it has three oxygen atoms bound together, and is represented as $O_3$. Ozone can be visualized as a regular oxygen molecule that has a very energetic, active, and excited companion, a single oxygen atom. Atomic oxygen ($O_1$) does not like to be alone and tries to use its energy to find a partner to bond or interact with. As a result, atomic oxygen will react with just about anything on contact. The atomic oxygen within ozone cannot be stable until it moves away from the $O_2$ molecule and forms a molecule with something else. If the atomic oxygen cannot find anything, it will eventually react with another oxygen atom that is in the same situation and they will stabilize each other, forming regular oxygen ($O_2$).

Such behavior makes ozone a very powerful oxidant. In chemistry, an oxidant is referred to as anything that oxidizes other compounds by transferring oxygen atoms to another molecule. For example, consider the following chemical reaction, which shows the reaction of ozone with carbon.

C(carbon)→2$O_3$(ozone)→$CO_2$(carbon dioxide)+2$O_2$ (oxygen)

This reaction indicates that one molecule of carbon reacts with two molecules of ozone to form one molecule of carbon dioxide along with two molecules of oxygen. In order to make sure the reaction is 100% complete we can allow the products of the reaction (the carbon dioxide and oxygen) to be removed from the reaction chamber, and then add some fresh ozone. This is a principle in chemistry called "Le Chatelier's principle," which ensures that even materials which might be stubborn to react with the ozone will gradually be coaxed to fully react and form harmless side products.

The decontamination process of the present disclosure may add humid/moist air to the ozonolysis process. Ozone reacts with water to form a number of different reactive chemicals, including "hydroxyl radical," "hydroperoxide radical," "superoxide radical ion," and "ozonide radical ion." Eventually, ozone in water will decompose over about 20-30 minutes and revert back to oxygen, but in the meantime, these different reactive chemicals help ozone to attack and decompose any other carbon-containing molecules that may be present. The exact mechanism by which ozone reacts in water when a potentially hazardous chemical (e.g., benzene, etc.) is present depends on the pollutant being attacked. It can perform reactions commonly referred to by chemists as "cyclo-addition," "electrophilic attack," or "nucleophilic attack." It can also work indirectly, by reacting with water first and using the resulting radicals (e.g., hydroxyl radical, hydroperoxide radical, superoxide radical ion, ozonide radical ion, etc.). Essentially, virtually any organic compound will, with enough exposure to ozone and moist air, fully oxidize to carbon dioxide and water.

Even for a simple molecule such as benzene, there can be a lot of chemical steps all happening at once when reacting with ozone. The reaction of ozone with benzene, however, can be summarized as follows:

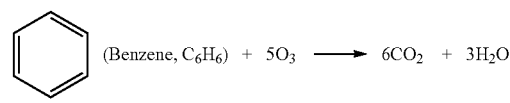

which shows that one molecule of benzene reacts with five molecules of ozone to form six molecules of carbon dioxide and three molecules of water. After ozone attacks benzene, the gases produced may be removed from a decontamination chamber of the ozone cleaning system and passed over or through a filter (e.g., a wire mesh that is coated with a titanium dioxide catalyst, etc.). As the gases flow through the filter, ultraviolet light may be shone into, on, etc. the filter. Similar to the reaction of the ozone layer of the Earth in the upper atmosphere with incoming sunlight, this treatment process ensures that any remaining ozone is destroyed before the harmless by-product gases are allowed to vent out of the decontamination chamber.

The example above for benzene is one of the simplest organic molecules, however, as mentioned above, there are other pollutants in our environment that are also dangerous such as benzopyrene, butadiene, formaldehyde, dibenzanthracene, trichloroethylene, tetrachloroethylene, polychlorinated biphenyls, etc. that the decontamination process of the ozone cleaning system can eliminate. Various decontamination processes are shown in the following chemical diagrams:

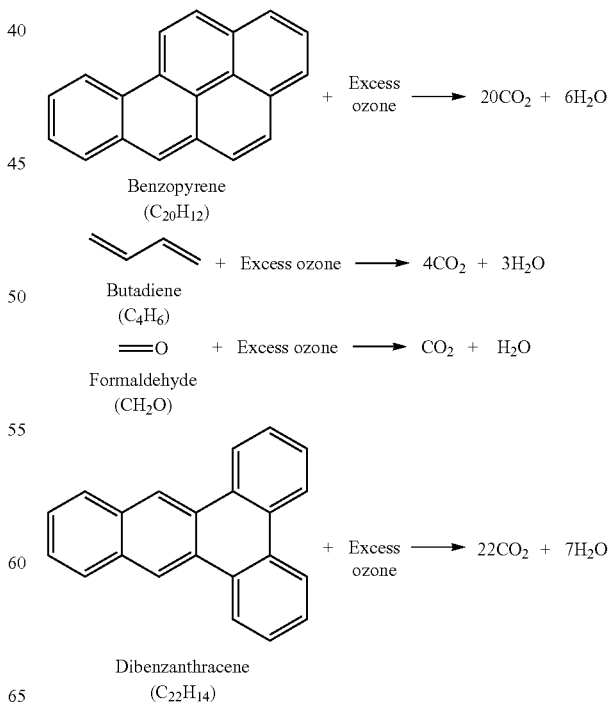

The ozone cleaning system may also be used to eradicate other toxins that contain chlorine, as shown in the following chemical diagrams:

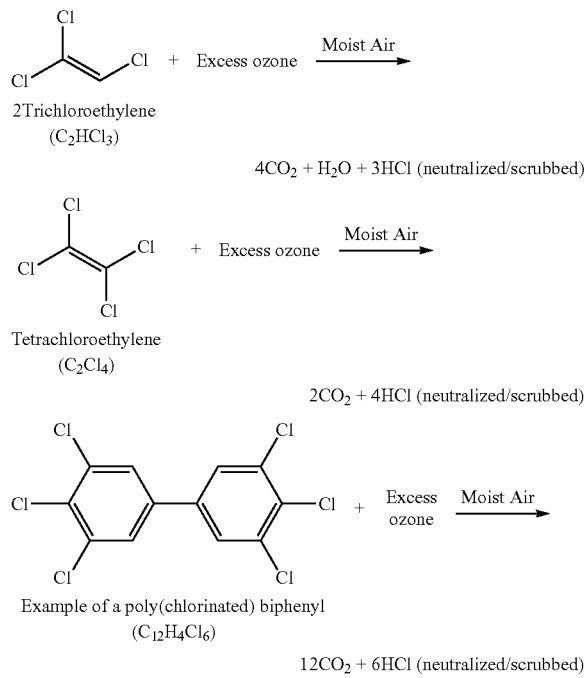

Accordingly, the ozone cleaning system is configured to implement a decontamination process to treat and break down extremely harmful pollutants with generated ozone, moisture, and/or ultraviolet light into carbon dioxide, water, and/or sodium chloride (i.e., table salt).

Ozone Cleaning System

Figure 2:
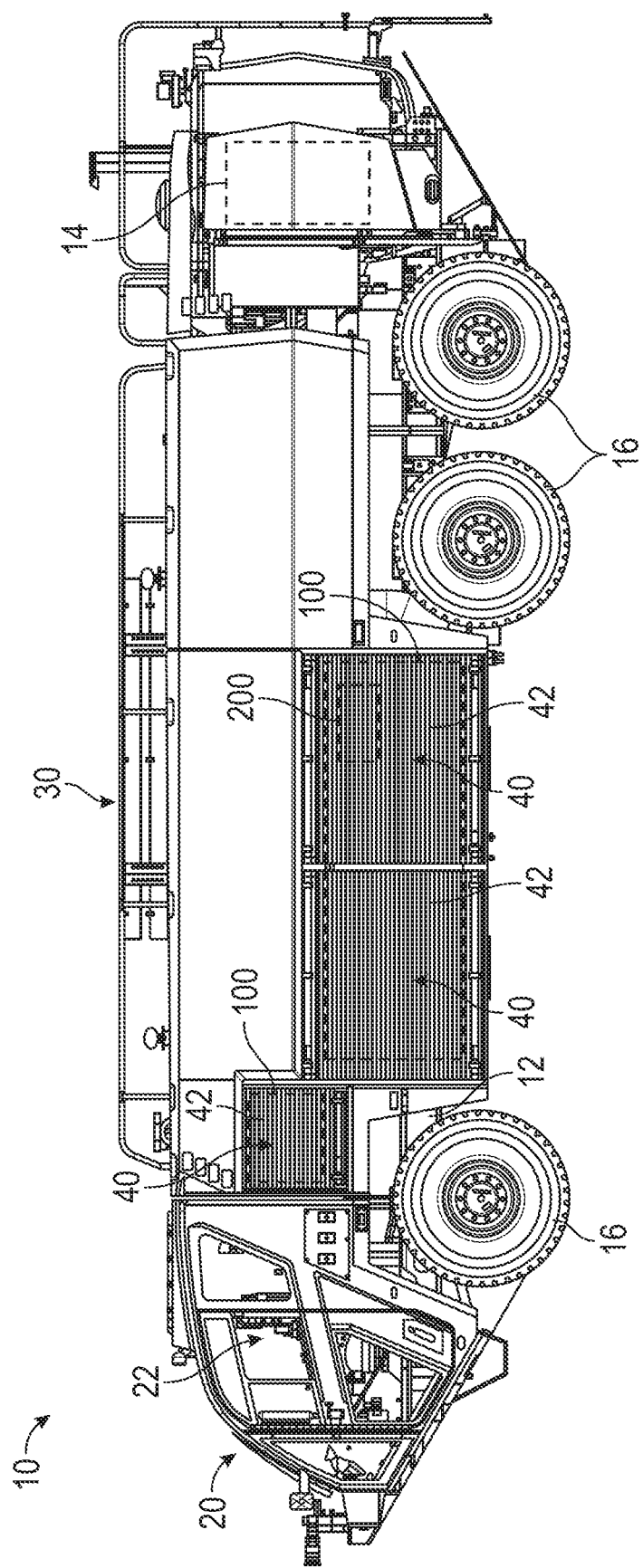
FIG. 2 is a perspective view of an airport fire fighting vehicle, according to an exemplary embodiment.

According to the exemplary embodiment shown in FIGS. 1 and 2, a vehicle, shown as vehicle 10, includes a cleaning system, shown as ozone cleaning system 100. The ozone cleaning system 100 may be configured neutralize organic carcinogens. In one embodiment, the ozone cleaning system 100 is a standalone unit that may be positioned within the vehicle 10, in a firehouse or station, and/or at any other suitable place the ozone cleaning system 100 may fit. In another embodiment, the ozone cleaning system 100 is integrated into the vehicle 10 (e.g., within a cab thereof, within a storage compartment thereof, etc.). The ozone cleaning system 100 may be capable of cleaning, disinfecting, and/or decontaminating loose items (e.g., fire fighting gear, etc.) and/or an interior of the vehicle 10.

According to the exemplary embodiment shown in FIG. 1, the vehicle 10 is configured as a single rear axle quint fire truck. In other embodiments, the vehicle 10 is configured as a tandem rear axles quint fire truck. In still other embodiments, the vehicle 10 is configured as another type of fire apparatus such as a tiller fire truck, an aerial platform fire truck, a mid-mount fire truck, etc. According to the exemplary embodiment shown in FIG. 2, the vehicle 10 is configured as an airport rescue fire fighting ("ARFF") truck. In other embodiments, the vehicle 10 is still another type of fire apparatus. In still other embodiments, the vehicle 10 is another type of vehicle (e.g., a refuse vehicle, a boom truck, a plow truck, a military vehicle, an ambulance, a police vehicle, etc.).

As shown in FIGS. 1 and 2, the vehicle 10 includes a chassis, shown as frame 12; a front cabin, shown as cab 20, coupled to the frame 12 (e.g., at a front end thereof, etc.) and defining an interior, shown as interior 22; and a rear assembly, shown as rear assembly 30, coupled to the frame 12 (e.g., at a rear end thereof, etc.). The cab 20 may include various components to facilitate operation of the vehicle 10 by an operator (e.g., a seat, a steering wheel, hydraulic controls, a user interface, switches, buttons, dials, etc.). The vehicle 10 includes a prime mover, shown as engine 14, coupled to the frame 12. As shown in FIG. 1, the engine 14 is positioned beneath the cab 20. As shown in FIG. 2, the engine 14 is positioned within the rear assembly 30 at the rear of the vehicle 10. As shown in FIGS. 1 and 2, the vehicle 10 includes a plurality of tractive elements, shown as wheel and tire assemblies 16. In other embodiments, the tractive elements include track elements. According to an exemplary embodiment, the engine 14 is configured to provide power to the wheel and tire assemblies 16 and/or to other systems of the vehicle 10 (e.g., a pneumatic system, a hydraulic system, etc.). The engine 14 may be configured to utilize one or more of a variety of fuels (e.g., gasoline, diesel, bio-diesel, ethanol, natural gas, etc.), according to various exemplary embodiments. According to an alternative embodiment, the engine 14 additionally or alternatively includes one or more electric motors coupled to the frame 12 (e.g., a hybrid vehicle, an electric vehicle, etc.). The electric motors may consume electrical power from an on-board storage device (e.g., batteries, ultra-capacitors, etc.), from an on-board generator (e.g., an internal combustion engine genset, etc.), and/or from an external power source (e.g., overhead power lines, etc.) and provide power to the systems of the vehicle 10.

As shown in FIGS. 1 and 2, the rear assembly 30 includes various compartments, shown as compartments 40. As shown in FIG. 2, the compartments 40 include doors, shown as doors 42. The doors 42 of the compartments 40 may be selectively opened to access an interior of the compartments 40. The interior of the compartments may store components of the vehicle 10, tools (e.g., fire fighting tools, etc.), and/or gear (e.g., fire fighting gear, etc.).

As shown in FIG. 1, the ozone cleaning system 100 is disposed within the interior 22 of the cab 20 of the vehicle 10. In such an embodiment, the ozone cleaning system 100 may be a standalone unit removable from the cab 20 and/or an integrated system within the cab 20. As shown in FIG. 2, the ozone cleaning system 100 is disposed in one or more of the compartments 40 of the vehicle 10. In such an embodiment, the ozone cleaning system 100 may be a standalone unit removable from the one or more compartments 40 and/or an integrated system within the one or more compartments 40. In embodiments where the ozone cleaning system 100 is a standalone unit, the ozone cleaning system 100 may be positioned at any suitable location (e.g., within a firehouse, a fire station, etc.).

Figure 3:
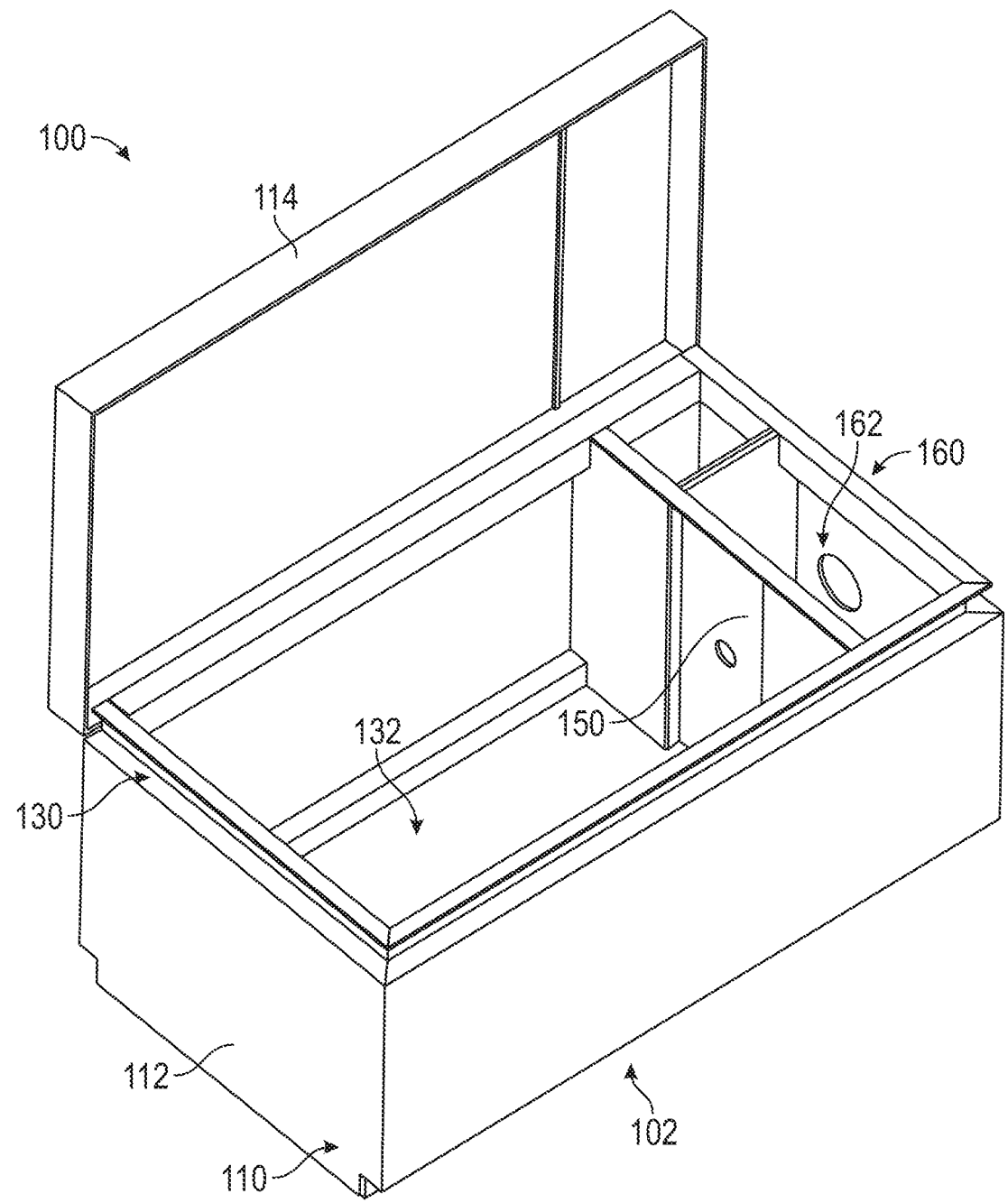
FIG. 3 is a perspective view of an ozone cleaning system, according to an exemplary embodiment.
Figure 4:
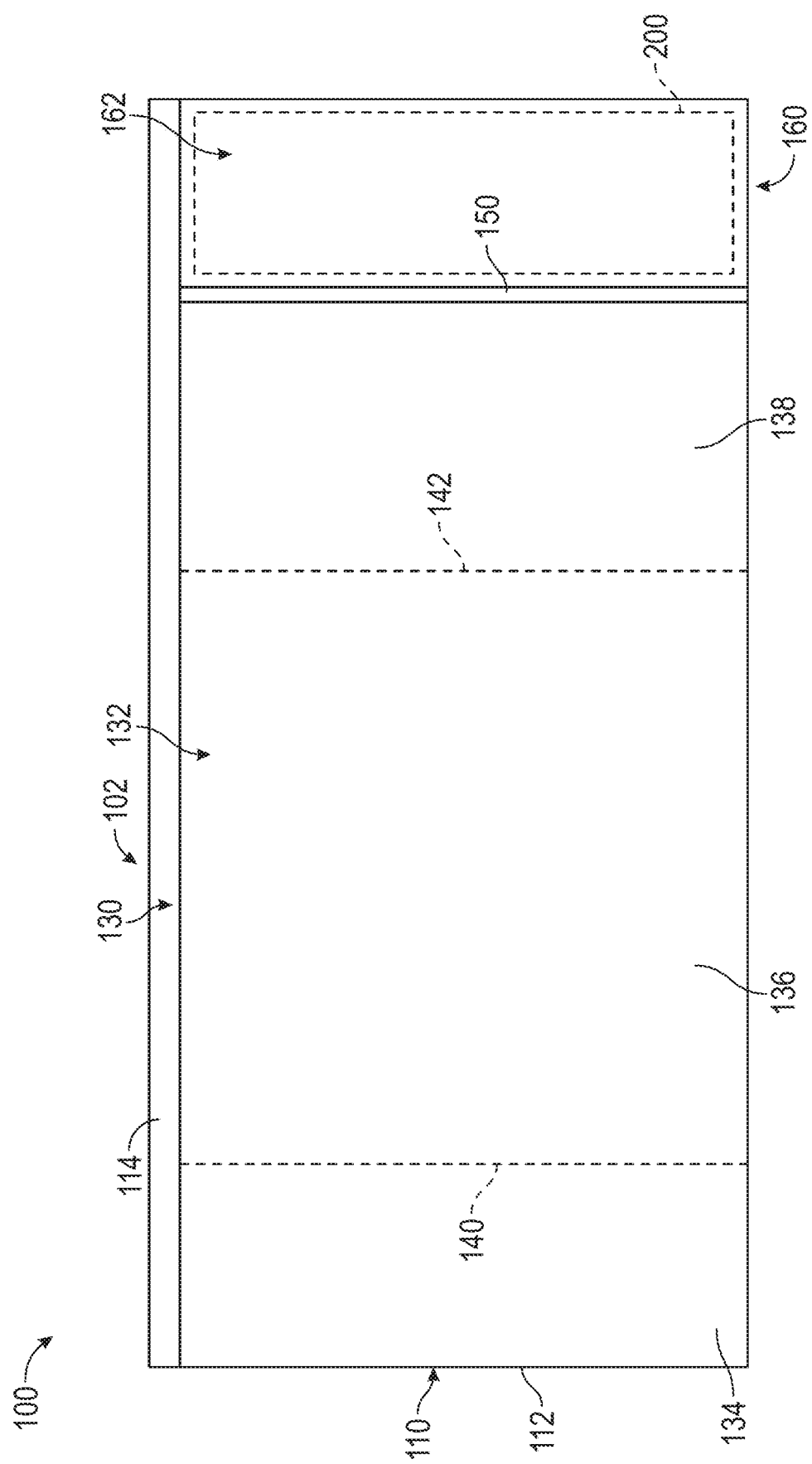
FIG. 4 is a side view of the ozone cleaning system of FIG. 3, according to an exemplary embodiment.
Figure 5:
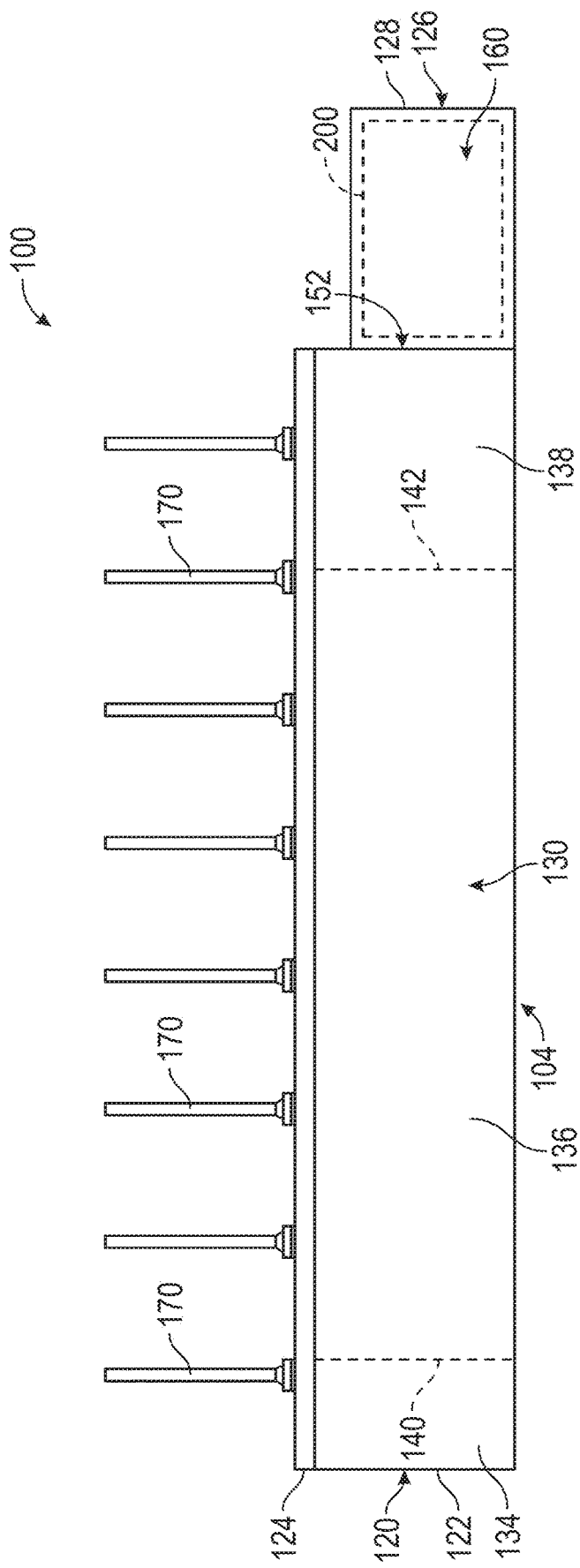
FIG. 5 is a side view of an ozone cleaning system, according to another exemplary embodiment.
Figure 6:
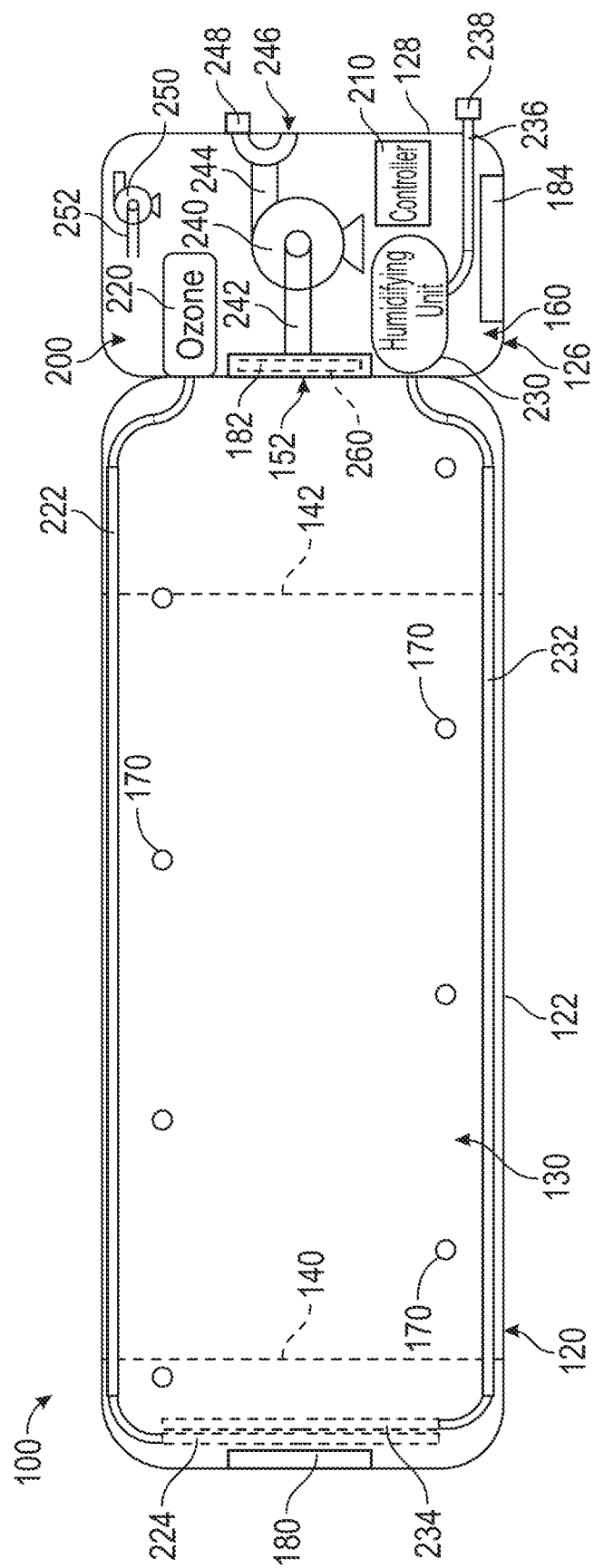
FIG. 6 is a top view of the ozone cleaning system of FIG. 5, according to an exemplary embodiment.

As shown in FIGS. 3 and 4, the ozone cleaning system 100 includes a first standalone unit, shown as gear decontamination unit ("GDU") 102. As shown in FIGS. 5 and 6, the ozone cleaning system 100 includes a second standalone unit, shown as GDU 104. As shown in FIG. 1, the GDU 102 and/or the GDU 104 are positioned within the interior 22 of the cab 20 of the vehicle 10. In other embodiments, the GDU 102 and/or the GDU 104 are positioned within the interior of the compartments 40 of the vehicle 10.

As shown in FIGS. 3 and 4, the GDU 102 includes a housing (e.g., a chest, a cabinet, a container, a locker, a bag, etc.), shown as housing 110. The housing 110 has a body, shown as body 112, that defines an interior chamber, and a cover (e.g., lid, door, etc.), shown as door 114, pivotally coupled to the body 112 to facilitate selectively accessing the interior chamber of the body 112. The interior chamber of the body 112 is separated into a first chamber, shown as decontamination chamber 130, and a second chamber, shown as utility chamber 160, by a wall, shown as dividing wall 150.

As shown in FIGS. 5 and 6, the GDU 104 includes a first housing (e.g., a chest, a cabinet, a container, a locker, a bag etc.), shown as decontamination housing 120, and a second housing, shown as utility housing 126, connected to the decontamination housing 120 at a junction, shown as connection 152. The decontamination housing 120 and the utility housing 126 may be integrally coupled (e.g., welded together, adhesively coupled together, etc.) and/or releasably coupled together (e.g., with fasteners, etc.). In some embodiments, the utility housing 126 and the components therein (e.g., blower, humidifier, lighting, filters, etc.) are an independent component or assembly for a retrofit kit that is useable with a pre-existing decontamination housing 120. The decontamination housing 120 has a body, shown as decontamination body 122, that defines the decontamination chamber 130 and a cover (e.g., lid, door, etc.), shown as decontamination chamber door 124, pivotally coupled to the decontamination body 122 to facilitate selectively accessing the decontamination chamber 130 of the decontamination body 122. The utility housing 126 has a body, shown as utility body 128, that defines the utility chamber 160. In some embodiments, the utility housing 126 has a utility chamber lid (e.g., similar to decontamination chamber door 124, etc.) pivotally coupled to the utility body 128 to facilitate selectively accessing the utility chamber 160 of the utility body 128.

As shown in FIGS. 3-6, the decontamination chamber 130 defines a cavity, shown as decontamination cavity 132. As shown in FIG. 3, the decontamination cavity 132 is a single, continuous cavity. According to an exemplary embodiment, the decontamination cavity 132 of the decontamination chamber 130 is configured to receive various gear, equipment, tools, etc. (e.g., boots, gloves, helmets, coats, pants, socks, shirts, etc.) to be decontaminated (e.g., to neutralize organic carcinogens disposed thereon, etc.). According to an exemplary embodiment, the decontamination chamber 130 is configured to be effectively sealed from an ambient environment such that a vacuum may be generated therein.

As shown in FIGS. 4-6, the decontamination cavity 132 is subdivided (e.g., separated, segregated, segmented, etc.) into a plurality of zones, shown as first decontamination zone 134, second decontamination zone 136, and third decontamination zone 138, by a plurality of dividers (e.g., walls, partitions, etc.), shown as first divider 140 and second divider 142. In other embodiments, the decontamination chamber 130 includes a different number of dividers (e.g., one, three, four, etc.) such that the decontamination cavity 132 is subdivided into a different number of decontamination zones (e.g., two, four, five, etc.). In one embodiment, the dividers (e.g., the first divider 140, the second divider 142, etc.) are at least partially permeable (e.g., define a plurality of apertures, manufactured from a permeable membrane, etc.). In another embodiment, the dividers are non-permeable. According to an exemplary embodiment, the dividers (e.g., the first divider 140, the second divider 142, etc.) facilitate separating various types of gear, equipment, tools, etc. within the decontamination cavity 132. By way of example, the first decontamination zone 134 may be configured to receive a first type of item (e.g., softer items such as gloves, shirts, socks, etc.), the second decontamination zone 136 may be configured to receive a second type of item (e.g., moderate items such as pants, jackets, etc.), and the third decontamination zone 138 may be configured to receive a third type of item (e.g., hard items such as boots, helmets, etc.).

As shown in FIGS. 3-6, the utility chamber 160 defines a cavity, shown as utility cavity 162. As shown in FIG. 4-6, the utility cavity 162 of the utility chamber 160 is configured to receive various components of a utility assembly, shown as utility assembly 200. According to an exemplary embodiment, the utility assembly 200 is configured to facilitate decontaminating and neutralizing organic carcinogens disposed on the items positioned within the decontamination cavity 132 of the decontamination chamber 130.

As shown in FIGS. 5 and 6, the GDU 104 includes a plurality of external posts (e.g., boot posts, glove posts, a helmet rack, etc.), shown as blower posts 170, extending from the decontamination chamber door 124 of the decontamination housing 120. In some embodiments, the GDU 104 does not include the blower posts 170. In some embodiments, the GDU 102 includes the blower posts 170 extending from the door 114 of the housing 110. In some embodiments, the compartments 40 include the blower posts 170. According to an exemplary embodiment, the blower posts 170 are configured to facilitate positioning boots, gloves, and/or helmets over them such that the blower posts 170 extend into the interiors thereof.

As shown in FIG. 6, the GDU 104 includes a plurality of filters variously positioned thereabout. It should be noted that the GDU 102 may include similar filters in similar locations. As shown in FIG. 6, the decontamination chamber 130 includes a first filter, shown as decontamination chamber inlet filter 180, positioned at the end of the decontamination chamber 130 opposite of the utility chamber 160. In other embodiments, the decontamination chamber inlet filter 180 is otherwise positioned. The decontamination chamber inlet filter 180 may selectively permit ambient air to flow into the decontamination chamber 130 from an ambient environment. The decontamination chamber inlet filter 180 may further filter debris, dirt, and other particulates from the ambient air.

As shown in FIG. 6, the decontamination chamber 130 and/or the utility chamber 160 include a second filter, shown as decontamination chamber outlet filter 182, positioned along the connection 152 (or the dividing wall 150 of the GDU 102) between the decontamination chamber 130 and the utility chamber 160. The decontamination chamber outlet filter 182 may selectively permit ozone or ozonated air to flow into the utility chamber 160 from the decontamination chamber 130. The decontamination chamber outlet filter 182 may further filter debris, dirt, and other particulates removed from the gear and/or equipment during the decontamination process. In some embodiments, the decontamination chamber outlet filter 182 includes a neutralizing compound, such as manganese dioxide ($MnO_2$), that is used to decompose the ozone or ozonated air to a more suitable form (e.g., from $O_3$ to $O_2$, etc.). In some embodiments, the decontamination chamber outlet filter 182 includes wire mesh coated with a titanium dioxide ($TiO_2$) catalyst. As shown in FIG. 6, the ozone cleaning system 100 includes a light source, shown as ultraviolet ("UV") lighting 260. According to an exemplary embodiment, the UV lighting 260 is positioned to shine light at, onto, into, etc. the decontamination chamber outlet filter 182 (e.g., to assist in breaking down excess ozone into oxygen, etc.).

As shown in FIG. 6, the utility chamber 160 includes a third filter, shown as utility chamber inlet filter 184. The utility chamber inlet filter 184 may selectively permit ambient air to flow into the utility chamber 160 from an ambient environment. The utility chamber inlet filter 184 may further filter debris, dirt, and other particulates from the ambient air.

Figure 7:
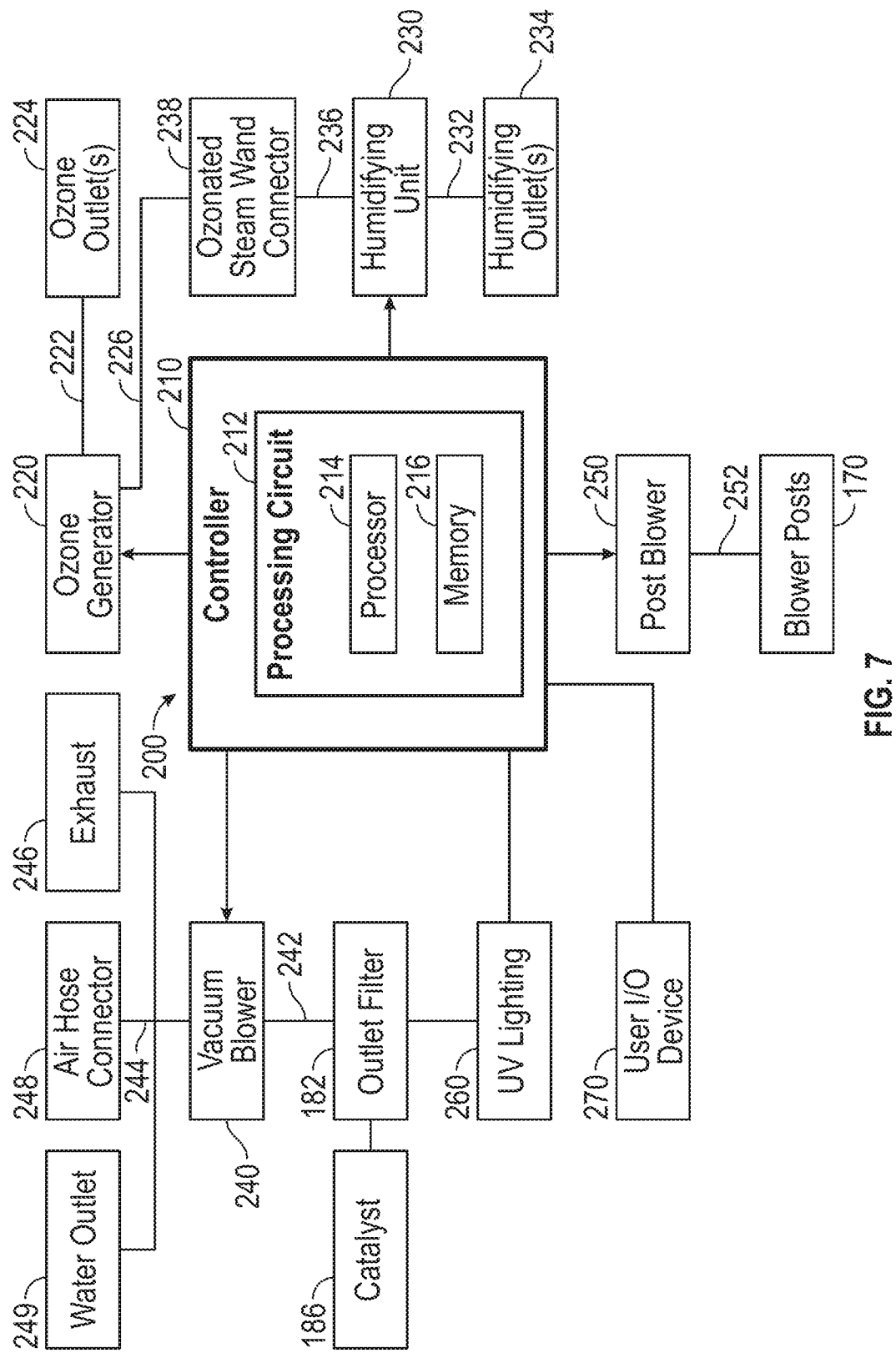
FIG. 7 is a schematic view of the ozone cleaning systems of FIGS. 3 and 5, according to an exemplary embodiment.

As shown in FIGS. 6 and 7, the utility assembly 200 includes a control system, shown as controller 210; a generator, shown as ozone generator 220; a humidifier, shown as humidifying unit 230; a first blower, shown as vacuum blower 240; a second blower, shown post blower 250; the UV lighting 260; and an input/output ("I/O") device, shown as user I/O device 270. In one embodiment, the controller 210 is configured to selectively engage, selectively disengage, control, and/or otherwise communicate with components of the utility assembly 200. As shown in FIG. 7, the controller 210 is coupled to the ozone generator 220, the humidifying unit 230, the vacuum blower 240, the post blower 250, the UV lighting 260, and the user I/O device 270. In other embodiments, the controller 210 is coupled to more or fewer components.

The controller 210 may be implemented as a general-purpose processor, an application specific integrated circuit (ASIC), one or more field programmable gate arrays (FPGAs), a digital-signal-processor (DSP), circuits containing one or more processing components, circuitry for supporting a microprocessor, a group of processing components, or other suitable electronic processing components. According to the exemplary embodiment shown in FIG. 7, the controller 210 includes a processing circuit 212 having a processor 214 and a memory 216. The processing circuit 212 may include an ASIC, one or more FPGAs, a DSP, circuits containing one or more processing components, circuitry for supporting a microprocessor, a group of processing components, or other suitable electronic processing components. In some embodiments, the processor 214 is configured to execute computer code stored in the memory 216 to facilitate the activities described herein. The memory 216 may be any volatile or non-volatile computer-readable storage medium capable of storing data or computer code relating to the activities described herein. According to an exemplary embodiment, the memory 216 includes computer code modules (e.g., executable code, object code, source code, script code, machine code, etc.) configured for execution by the processor 214.

As shown in FIGS. 4-6, at least a portion of the utility assembly 200 is disposed within the utility chamber 160 of the GDU 102 and the GDU 104 (e.g., the ozone cleaning system 100 is a standalone unit, etc.). As shown in FIG. 2, the utility assembly 200 is disposed within one or more of the compartments 40 of the rear assembly 30. In such an embodiment, the utility assembly 200 may be integrated directly into one or more of the compartments 40 such that the ozone cleaning system 100 does not include the GDU 102 or the GDU 104. Further, in such an embodiment, the one or more compartments 40 may function as the decontamination chamber 130 (e.g., including or not including the dividers, etc.). In another embodiment, the utility assembly 200 is disposed within the interior 22 of the cab 20. In such an embodiment, the utility assembly 200 may be integrated directly into the interior 22 of the cab 20 such that the ozone cleaning system 100 does not include the GDU 102 or the GDU 104, and is configured to facilitate decontaminating and neutralizing organic carcinogens disposed within the interior 22 of the cab 20.

According to an exemplary embodiment, the ozone generator 220 is configured to generate ozone (e.g., trioxygen, $O_3$, etc.) to be injected into the decontamination cavity 132 of the decontamination chamber 130. As shown in FIGS. 6 and 7, the ozone generator 220 includes a first conduit, shown as ozone conduit 222, having at least one outlet, shown as ozone outlets 224. As shown in FIG. 6, the ozone conduit 222 extends from the utility chamber 160 through the decontamination chamber 130 with a single ozone outlet 224 positioned at the end of the decontamination chamber 130 opposite the utility chamber 160. A single ozone outlet 224 may be used in embodiments where (i) the GDU 102, the GDU 104, and/or the compartments 40 do not include the dividers (e.g., the first divider 140, the second divider 142, etc.) and/or (ii) the dividers are at least partially permeable.

In some embodiments, the ozone conduit 222 includes a plurality of ozone outlets 224 positioned along the length thereof. A plurality of ozone outlets 224 may be used in embodiments where the GDU 102, the GDU 104, and/or the compartments 40 do or do not include the dividers (e.g., the first divider 140, the second divider 142, etc.). By way of example, the plurality of ozone outlets 224 may be positioned uniformly and/or non-uniformly along the length of the ozone conduit 222 such that the ozone may be injected throughout the decontamination chamber 130. By way of another example, the ozone conduit 222 may include a first ozone outlet 224 (or a first set of ozone outlets 224) positioned to facilitate injecting ozone into the first decontamination zone 134, a second ozone outlet 224 (or a second set of ozone outlets 224) positioned to facilitate injecting ozone into the second decontamination zone 136, and a third ozone outlet 224 (or a third set of ozone outlets 224) positioned to facilitate injecting ozone into the third decontamination zone 138. In some embodiments, the ozone generator 220 includes a plurality of ozone conduits 222, each having a respective ozone outlet 224. By way of example, a first ozone conduit 222 having a first ozone outlet 224 (or a first set of ozone outlets 224) may extend from the ozone generator 220 into the first decontamination zone 134 to facilitate injecting ozone into the first decontamination zone 134, a second ozone conduit 222 having a second ozone outlet 224 (or a second set of ozone outlets 224) may extend from the ozone generator 220 into the second decontamination zone 136 to facilitate injecting ozone into the second decontamination zone 136, and a third ozone conduit 222 having a third ozone outlet 224 (or a third set of ozone outlets 224) may extend from the ozone generator 220 into the third decontamination zone 138 to facilitate injecting ozone into the third decontamination zone 138. In embodiments where the decontamination zones (e.g., the first decontamination zone 134, the second decontamination zone 136, the third decontamination zone 138, etc.) have a designated ozone outlet 224 associated therewith, the ozone generator 220 may be configured to facilitate providing different concentrations of ozone to each respective decontamination zone (e.g., based on the type of equipment disposed therein, using controllable valves, controlled by the controller 210, etc.).

According to an exemplary embodiment, the humidifying unit 230 is configured to generate humidity (e.g., moisture, mist, moist air, etc.) to be injected into the decontamination cavity 132 of the decontamination chamber 130. As shown in FIGS. 6 and 7, the humidifying unit 230 includes a first conduit, shown as humidity conduit 232, having at least one outlet, shown as humidity outlets 234. As shown in FIG. 6, the humidity conduit 232 extends from the utility chamber 160 through the decontamination chamber 130 with a single humidity outlet 234 positioned at the end of the decontamination chamber 130 opposite the utility chamber 160. A single humidity outlet 234 may be used in embodiments where (i) the GDU 102, the GDU 104, and/or the compartments 40 do not include the dividers (e.g., the first divider 140, the second divider 142, etc.) and/or (ii) the dividers are at least partially permeable.

In some embodiments, the humidity conduit 232 includes a plurality of humidity outlets 234 positioned along the length thereof. A plurality of humidity outlets 234 may be used in embodiments where the GDU 102, the GDU 104, the compartments 40 do or do not include the dividers (e.g., the first divider 140, the second divider 142, etc.). By way of example, the plurality of humidity outlets 234 may be positioned uniformly and/or non-uniformly along the length of the humidity conduit 232 such that the humidity may be injected throughout the decontamination chamber 130. By way of another example, the humidity conduit 232 may include a first humidity outlet 234 (or a first set of humidity outlets 234) positioned to facilitate injecting humidity into the first decontamination zone 134, a second humidity outlet 234 (or a second set of humidity outlets 234) positioned to facilitate injecting humidity into the second decontamination zone 136, and a third humidity outlet 234 (or a third set of humidity outlets 234) positioned to facilitate injecting humidity into the third decontamination zone 138. In some embodiments, the humidifying unit 230 includes a plurality of humidity conduits 232, each having a respective humidity outlet 234. By way of example, a first humidity conduit 232 having a first humidity outlet 234 (or a first set of humidity outlets 234) may extend from the humidifying unit 230 into the first decontamination zone 134 to facilitate injecting humidity into the first decontamination zone 134, a second humidity conduit 232 having a second humidity outlet 234 (or a second set of humidity outlets 234) may extend from the humidifying unit 230 into the second decontamination zone 136 to facilitate injecting humidity into the second decontamination zone 136, and a third humidity conduit 232 having a third humidity outlet 234 (or a third set of humidity outlets 234) may extend from the humidifying unit 230 into the third decontamination zone 138 to facilitate injecting humidity into the third decontamination zone 138. In embodiments where the decontamination zones (e.g., the first decontamination zone 134, the second decontamination zone 136, the third decontamination zone 138, etc.) have a designated humidity outlet 234 associated therewith, the humidifying unit 230 may be configured to facilitate providing different concentrations of humidity to each respective decontamination zone (e.g., based on the type of equipment disposed therein, using controllable valves, controlled by the controller 210, etc.).

As shown in FIGS. 6 and 7, the ozone generator 220 includes a second conduit, shown as ozone conduit 226, and the humidifying unit 230 includes a second conduit, shown as humidity conduit 236, that couple to a first connector (e.g., a snap-fit connector, a screw connector, a quick-release connector, a nozzle, etc.), shown as ozonated steam wand connector 238. According to an exemplary embodiment, the ozonated steam wand connector 238 is configured to facilitate releasably coupling a hand wand device to the utility assembly 200. The hand wand device may be used by an operator to manually decontaminate gear and/or equipment external to the GDU 102, the GDU 104, and/or the compartments 40 (e.g., similar to using a clothes steamer, etc.).

As shown in FIGS. 6 and 7, the vacuum blower 240 includes a first conduit, shown as inlet conduit 242, coupled to the decontamination chamber outlet filter 182. According to an exemplary embodiment, the vacuum blower 240 is configured to (i) pull ambient air into the decontamination chamber 130 (e.g., through the decontamination chamber inlet filter 180, etc.), (ii) generate a vacuum within the decontamination chamber 130 at the start of the decontamination process (e.g., by pulling air from within the decontamination chamber 130 through the decontamination chamber outlet filter 182, etc.), and/or (iii) pull ozone, ozonated air, carbon dioxide, water moisture, sodium chloride, etc., from the decontamination chamber 130 at the end of the decontamination process (e.g., through the decontamination chamber outlet filter 182, etc.). In some embodiments, the vacuum blower 240 includes a plurality of inlet conduits 242 (e.g., in embodiments where the dividers are not permeable, etc.). By way of example, a first inlet conduit 242 may extend from the vacuum blower 240 into the first decontamination zone 134, a second inlet conduit 242 may extend from the vacuum blower 240 into the second decontamination zone 136, and a third inlet conduit 242 may extend from the vacuum blower 240 into the third decontamination zone 138.

As shown in FIGS. 6 and 7, the vacuum blower 240 includes a second conduit, shown as outlet conduit 244, that couples to a first outlet, shown as exhaust 246, a second connector (e.g., a snap-fit connector, a screw connector, a quick-release connector, a nozzle, etc.), shown as air hose connector 248, and/or a second outlet, shown as water outlet 249. According to an exemplary embodiment, the air hose connector 248 is configured to facilitate releasably coupling an air hose to the utility assembly 200. The air hose may extend from the air hose connector 248 to the exterior of the vehicle 10 (e.g., exterior of the cab 20, the compartments 40, etc.) or to the exterior of a firehouse. According to an exemplary embodiment, the vacuum blower 240 is configured to provide the gases pulled through the inlet conduit 242 from the decontamination chamber 130 to the outlet conduit 244 to be dispelled from the ozone cleaning system 100 (e.g., the GDU 102, the GDU 104, the compartments 40, the cab 20, etc.) to the ambient environment (e.g., external to the cab 20, external to the compartments 40, etc.). In some embodiments, the air is dispelled through the exhaust 246 directly to the ambient environment. In some embodiments, the exhaust 246 is coupled to a reservoir (e.g., a tank, etc.) configured to store the exhausted air (e.g., for disposal at a designated location, etc.). In some embodiments, the air is dispelled through the air hose connector 248 to the air hose such that the air is dispelled external from the cab 20 and/or the compartments 40.

According to an exemplary embodiment, the water outlet 249 is configured to facilitate dispelling or collecting water, moisture, humidity, etc. that is pulled from the decontamination chamber 130 as a result of the decontamination process. In one embodiment, the water outlet 249 is configured as a drain than expels the water from the ozone cleaning system 100 (e.g., out of the vehicle 10, out of a fire house, out of the GDU 102, out of the GDU 104, etc.). In another embodiment, the water outlet 249 is a tank or reservoir that collects the water, moisture, humidity, etc. pulled from the decontamination chamber 130 as a result of the decontamination process and may then be selectively emptied by an operator.

As shown in FIGS. 6 and 7, the post blower 250 includes a conduit, shown as post conduit 252. According to an exemplary embodiment, the post conduit 252 extends from the post blower 250 to the blower posts 170. The post blower 250 may be configured to provide ambient air, ozone, and/or humidity to the items (e.g., boots, gloves, helmets, etc.) positioned on the blower posts 170 to facilitate drying and/or decontaminating the items.

Figure 8:
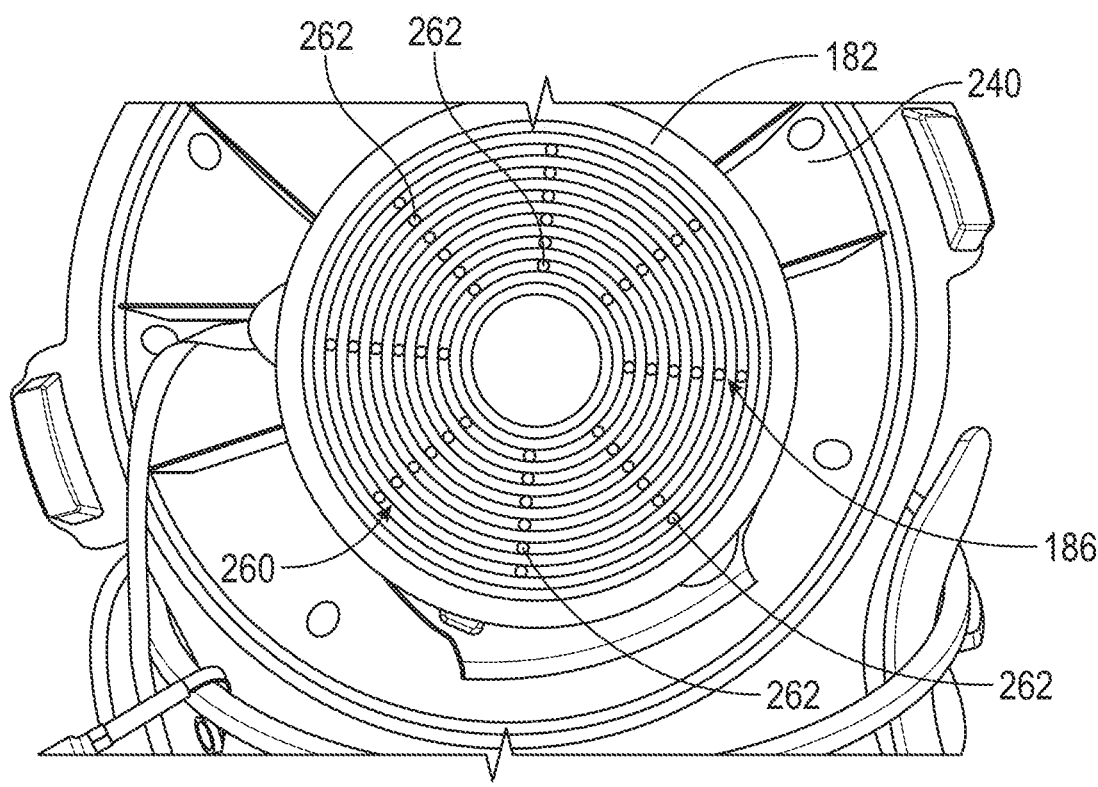
FIG. 8 is a detailed view of a photocatalytic oxidation filter of the ozone cleaning systems of FIGS. 3 and 5, according to an exemplary embodiment.

As shown in FIGS. 6-8, the UV lighting 260 is positioned proximate (e.g., next to, in contact with, intertwined with, adjacent to, etc.) the decontamination chamber outlet filter 182 having a catalyst, shown as titanium dioxide catalyst 186. As shown in FIG. 8, the UV lighting 260 includes a plurality of lighting elements, shown as light emitting diodes (LEDs) 262. According to an exemplary embodiment, the UV lighting 260 (e.g., the LEDs 262, etc.) and decontamination chamber outlet filter 182 (e.g., the titanium dioxide catalyst 186, etc.) form a photocatalytic oxidation filter. According to an exemplary embodiment, the LEDs 262 are positioned to provide UV light that interacts with the titanium dioxide catalyst 186 of the decontamination chamber outlet filter 182 to initiate a photocatalysis process on the organic compounds (e.g., carcinogens, etc.) and/or excess ozone flowing therethrough (e.g., as a result of the decontamination process applied to the gear, cab, etc.) to break down any remaining organic compounds and/or excess ozone (e.g., into oxygen, carbon dioxide, water, sodium chloride, etc.; to prevent exhausting such contaminants into the environment; etc.).

Figure 9:
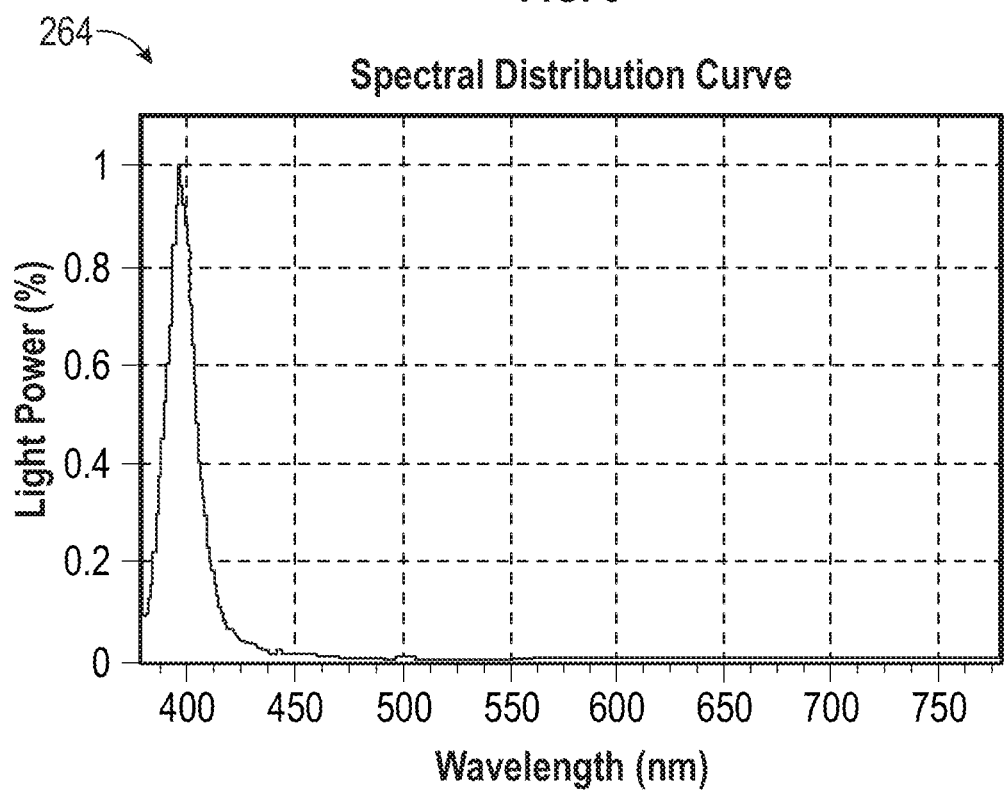
FIG. 9 is a graph of a spectral distribution curve for a light source of the photocatalytic oxidation filter of FIG. 8, according to an exemplary embodiment.

As shown in FIG. 9, the LEDs 262 have a spectral distribution curve 264 for the UV light emitted therefrom. According to an exemplary embodiment, the LEDs 262 have a wavelength spectrum of approximately 250 nm to 415 nm, with a peak wavelength at approximately 395 nm. According to an exemplary embodiment, the target wavelength for photoactivation of the titanium dioxide catalyst 186 is approximately 388 nm and the titanium dioxide catalyst 186 has a particle size around 20 nm. In other embodiments, the LEDs 262 and/or the titanium dioxide catalyst 186 have differing characteristics.

According to an exemplary embodiment, the user I/O device 270 is configured to facilitate (i) providing inputs (e.g., information, commands, etc.) to the controller 210 and/or (ii) providing outputs (e.g., feedback, status information, etc.) to an operator of the ozone cleaning system 100. The user I/O device 270 may include a display screen configured to provide a graphical user interface ("GIU") to an operator thereof and/or facilitate receiving touch inputs or commands. The user I/O device 270 may additionally or alternatively include various analog control features such as buttons, switches, dials, etc. An operator may provide commands or information to the controller 210 with the user I/O device 270 such as an indication of a type or types of equipment disposed in the decontamination chamber 130, an indication of a desired decontamination time, an indication of an amount of the decontamination chamber 130 that is full (e.g., a small sized load, a medium sized load, a large sized load, etc.), an indication of an amount of ozone to inject, an indication of an amount of humidity to inject, a selection of a predefined decontamination mode, a command to start and/or stop a decontamination cycle, a command to operate the post blower 250, etc. The controller 210 may be configured to provide feedback to the operator with the user I/O device 270 such as an indication of a remaining time left in a decontamination cycle, an indication when the decontamination cycle is completed (e.g., visual, audible, etc.), etc.

The controller 210 may be configured to control operation of the ozone generator 220. By way of example, the controller 210 may be configured to control whether ozone is generated by and/or an amount of ozone injected into the decontamination chamber 130 or the cab 20 by the ozone generator 220 (e.g., based on a selected decontamination mode, based on operator inputs received from the user I/O device 270, etc.). By way of another example, the controller 210 may be configured to control an amount or concentration of ozone injected into each zone (e.g., the first decontamination zone 134, the second decontamination zone 136, the third decontamination zone 138, etc.) of the decontamination chamber 130.

The controller 210 may be configured to control operation of the humidifying unit 230. By way of example, the controller 210 may be configured to control whether humidity is generator by and/or an amount or concentration of humidity injected into the decontamination chamber 130 or the cab 20 by the humidifying unit 230 (e.g., based on a selected decontamination mode, based on operator inputs received from the user I/O device 270, etc.). By way of another example, the controller 210 may be configured to control an amount of humidity injected into each zone (e.g., the first decontamination zone 134, the second decontamination zone 136, the third decontamination zone 138, etc.) of the decontamination chamber 130. The controller 210 may also be configured to activate the ozonated steam wand connector 238.

The controller 210 may be configured to control operation of the vacuum blower 240. By way of example, the controller 210 may be configured to control when the vacuum blower 240 is active and when the vacuum blower 240 is not active (e.g., based on a selected decontamination mode, based on operator inputs received from the user I/O device 270, etc.). The controller 210 may also be configured to activate the air hose connector 248.

The controller 210 may be configured to control operation of the post blower 250. By way of example, the controller 210 may be configured to control when the post blower 250 is active and when the post blower 250 is not active (e.g., based on a selected decontamination mode, based on operator inputs received from the user I/O device 270, etc.).

The controller 210 may be configured to control operation of the UV lighting 260. By way of example, the controller 210 may be configured to control when the LEDs 262 are on and when the LEDs 262 are off (e.g., based on a selected decontamination mode, based on operator inputs received from the user I/O device 270, following the decontamination process and the initiation of the photocatalysis process, etc.).

According to an exemplary embodiment, the vacuum blower 240 is controlled by the controller 210 to form a vacuum within the decontamination chamber 130 or the cab 20 to cause contaminants to desorb from the gear within the decontamination chamber 130 or the interior 22 of the cab 20, respectively, and outgas into the surrounding chamber. The ozone generator 220 and the humidifying unit 230 are controlled by the controller 210 to provide ozone and moisture, respectively, into the surrounding chamber to break down the contaminants by oxidizing the contaminates into carbon dioxide, water, and sodium chloride. The longer the exposure to the ozone and moisture, the more that the contaminants may be broken down. The vacuum blower 240 is then controlled by the controller 210 to draw (i) any remaining ozone and contaminants and (ii) the resulting carbon dioxide, oxygen, water, and/or sodium chloride through the decontamination chamber outlet filter 182. The LEDs 262 are activated by the controller 210 such that the UV light emitted therefrom interacts with the titanium dioxide catalyst 186 of the decontamination chamber outlet filter 182 to initiate the photocatalysis process on any remaining ozone and contaminants flowing therethrough to break down (e.g., oxidize, etc.) the remaining ozone and organic contaminants into oxygen and other harmless compounds (e.g., carbon dioxide, water, sodium chloride, etc.). According to an exemplary embodiment, the application of the vacuum and the UV lighting in the decontamination process facilitates significantly reducing (i) the amount of ozone that the gear and/or the interior 22 of the cab 20 need to be exposed to and (ii) the time of exposure that the gear and/or the interior 22 of the cab 20 need to be exposed to ozone to be completely or substantially completely decontaminated. By reducing the amount and time of ozone exposure, the ozone has a reduced negative impact on the materials being decontaminated (e.g., leading to longer use life, less wear, etc.).

Figure 10:
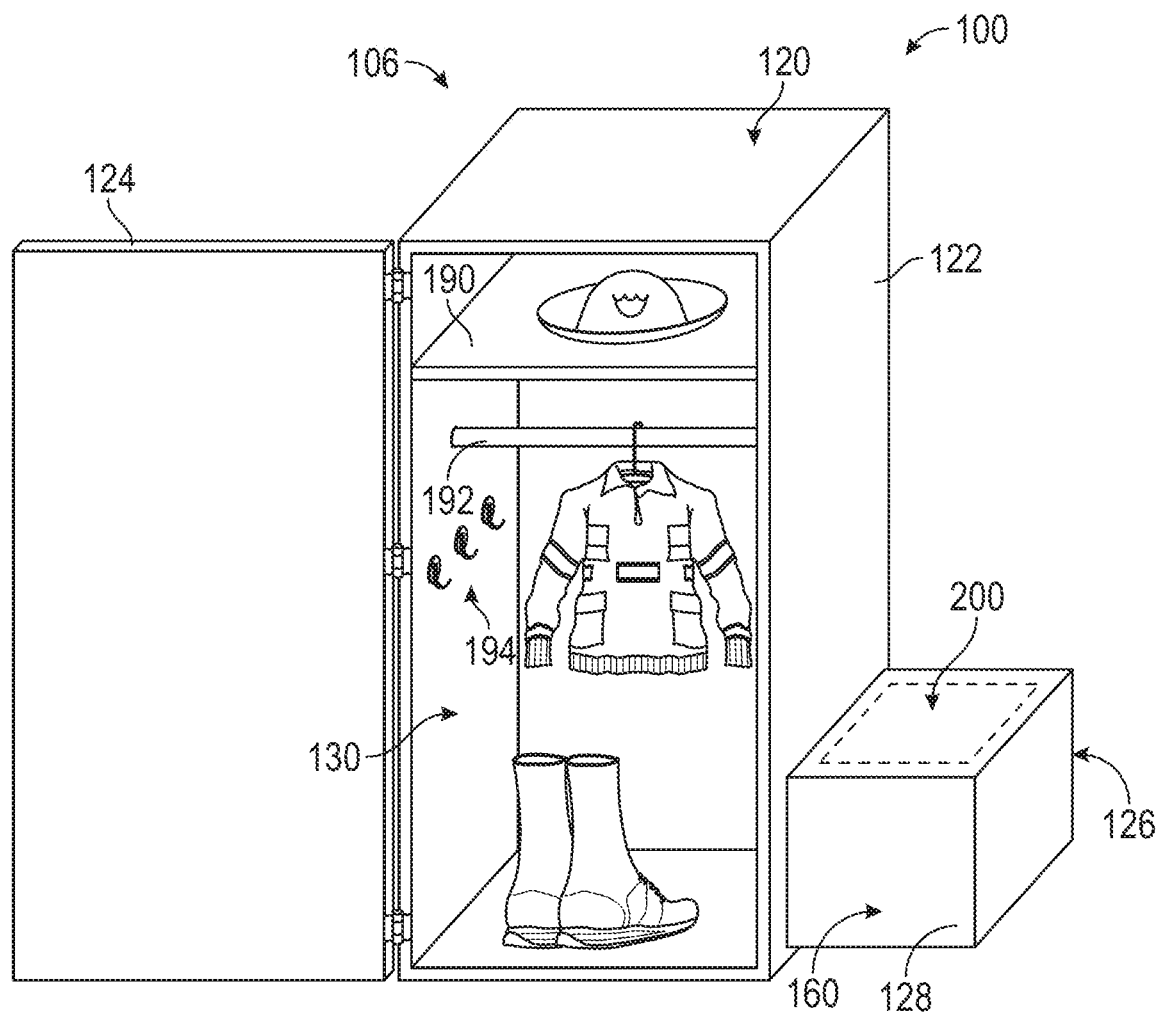
FIG. 10 is a perspective view of an ozone cleaning system, according to another exemplary embodiment.

As shown in FIG. 10, the ozone cleaning system 100 includes a third standalone unit, shown as GDU 106. According to the exemplary embodiment shown as in FIG. 10, the GDU 106 is a vertical GDU similar to a portable/external closet, armoire, large safe, etc. As shown in FIG. 10, the GDU 106 includes similar components as the GDU 102 and/or the GDU 104, which includes (i) the decontamination housing 120 having the decontamination body 122 that defines the decontamination chamber 130, (ii) the decontamination chamber door 124 positioned to selectively enclose the decontamination chamber 130, (iii) the utility housing 126 having the utility body 128 coupled to the decontamination body 122, and (iv) the utility assembly 200 disposed within the utility chamber 160 of the utility body 128. In other embodiments, the utility assembly 200 is positioned internally within the decontamination chamber 130 of the decontamination body 122 (e.g., similar to GDU 102, etc.). As shown in FIG. 10, the GDU 106 includes various storage elements, shown as shelving 190, hanger rack 192, and hanging hooks 194. The shelving 190 may be configured to support various gear (e.g., firefighting hats, gloves, etc.) that are to be decontaminated by the GDU 106. The hanger rack 192 and/or the hanging hooks 194 may be configured to facilitate hanging jackets, pants, shirts, and/or other hangable gear within the decontamination chamber 130 for decontamination (e.g., which is facilitated by the elongated height of the GDU 106 relative to the GDU 102 and the GDU 104, etc.). The base or floor of the decontamination chamber 130 may also be configured to support various gear (e.g., firefighting boots, etc.) that are to be decontaminated by the GDU 106. In some embodiments, the GDU 106 includes other components to support and/or organize gear therein.

Figure 11:
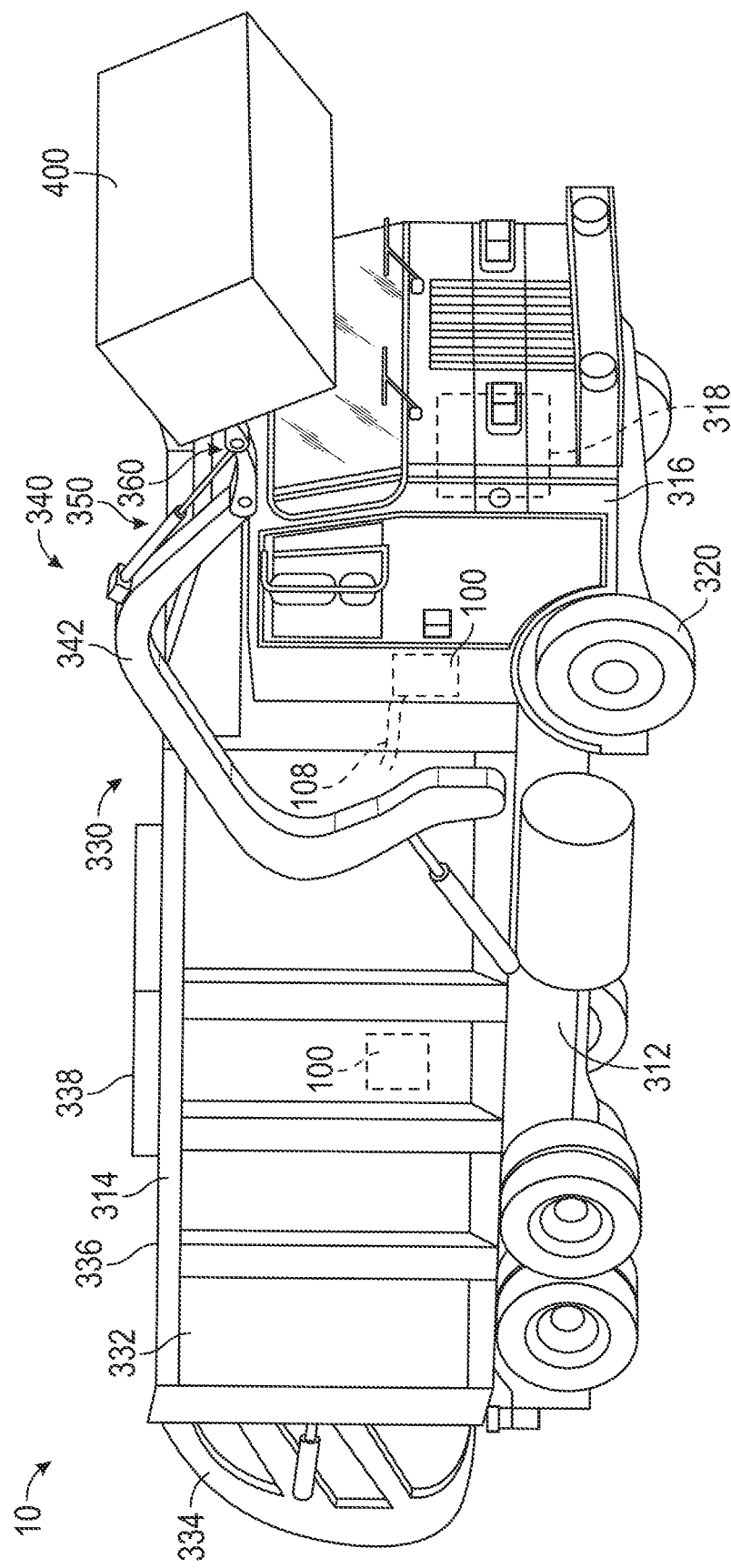
FIG. 11 is a perspective view of a refuse vehicle, according to an exemplary embodiment.

According to the exemplary embodiment shown in FIG. 11, the vehicle 10 is configured as a front-loading refuse truck (e.g., a garbage truck, a waste collection truck, a sanitation truck, etc.). In other embodiments, the vehicle 10 is configured as a side-loading refuse truck or a rear-loading refuse truck. As shown in FIG. 11, the vehicle 10 includes a chassis, shown as frame 312; a body assembly, shown as body 314, coupled to the frame 312 (e.g., at a rear end thereof, etc.); and a cab, shown as cab 316, coupled to the frame 312 (e.g., at a front end thereof, etc.). The cab 316 may include various components to facilitate operation of the vehicle 10 by an operator (e.g., a seat, a steering wheel, hydraulic controls, a user interface, switches, buttons, dials, etc.). As shown in FIG. 11, the vehicle 10 includes a prime mover, shown as engine 318, coupled to the frame 312 at a position beneath the cab 316. The engine 318 is configured to provide power to a plurality of tractive elements, shown as wheels 320, and/or to other systems of the vehicle 10 (e.g., a pneumatic system, a hydraulic system, etc.). The engine 318 may be configured to utilize one or more of a variety of fuels (e.g., gasoline, diesel, bio-diesel, ethanol, natural gas, etc.), according to various exemplary embodiments. According to an alternative embodiment, the engine 318 additionally or alternatively includes one or more electric motors coupled to the frame 312 (e.g., a hybrid refuse vehicle, an electric refuse vehicle, etc.). The electric motors may consume electrical power from an on-board storage device (e.g., batteries, ultra-capacitors, etc.), from an on-board generator (e.g., an internal combustion engine, etc.), and/or from an external power source (e.g., overhead power lines, etc.) and provide power to the systems of the vehicle 10.

According to an exemplary embodiment, the vehicle 10 is configured to transport refuse from various waste receptacles within a municipality to a storage and/or processing facility (e.g., a landfill, an incineration facility, a recycling facility, etc.). As shown in FIG. 11, the body 314 includes a plurality of panels, shown as panels 332, a tailgate 334, and a cover 336. The panels 332, the tailgate 334, and the cover 336 define a collection chamber (e.g., hopper, etc.), shown as refuse compartment 330. Loose refuse may be placed into the refuse compartment 330 where it may thereafter be compacted. The refuse compartment 330 may provide temporary storage for refuse during transport to a waste disposal site and/or a recycling facility. In some embodiments, at least a portion of the body 314 and the refuse compartment 330 extend in front of the cab 316. According to the embodiment shown in FIG. 11, the body 314 and the refuse compartment 330 are positioned behind the cab 316. In some embodiments, the refuse compartment 330 includes a hopper volume and a storage volume. Refuse may be initially loaded into the hopper volume and thereafter compacted into the storage volume. According to an exemplary embodiment, the hopper volume is positioned between the storage volume and the cab 316 (i.e., refuse is loaded into a position of the refuse compartment 330 behind the cab 316 and stored in a position further toward the rear of the refuse compartment 330). In other embodiments, the storage volume is positioned between the hopper volume and the cab 316 (e.g., a rear-loading refuse vehicle, etc.).

As shown in FIG. 11, the vehicle 10 includes a lift mechanism/system (e.g., a front-loading lift assembly, etc.), shown as lift assembly 340. The lift assembly 340 includes a pair of arms, shown as lift arms 342, coupled to the frame 312 and/or the body 314 on either side of the vehicle 10 such that the lift arms 342 extend forward of the cab 316 (e.g., a front-loading refuse vehicle, etc.). In other embodiments, the lift assembly 340 extends rearward of the body 314 (e.g., a rear-loading refuse vehicle, etc.). In still other embodiments, the lift assembly 340 extends from a side of the body 314 (e.g., a side-loading refuse vehicle, etc.). The lift arms 342 may be rotatably coupled to frame 312 with a pivot (e.g., a lug, a shaft, etc.). As shown in FIG. 11, the lift assembly 340 includes first actuators, shown as lift arm actuators 344 (e.g., hydraulic cylinders, etc.), coupled to the frame 312 and the lift arms 342. The lift arm actuators 344 are positioned such that extension and retraction thereof rotates the lift arms 342 about an axis extending through the pivot, according to an exemplary embodiment.

As shown in FIG. 11, the vehicle 10 includes forks, shown as lift forks 360, coupled to the lift arms 342 of the lift assembly 340. The lift forks 360 are configured to engage with a container, shown as refuse container 400, to selectively and releasably secure the refuse container 400 to the lift assembly 340. As shown in FIG. 11, the lift arms 342 are rotated by the lift arm actuators 344 to lift the refuse container 400 over the cab 316. The lift assembly 340 includes second actuators, shown as articulation actuators 350 (e.g., hydraulic cylinders, etc.). According to an exemplary embodiment, the articulation actuators 350 are positioned to articulate the lift forks 360. Such articulation may assist in tipping refuse out of the refuse container 400 and into the hopper volume of the refuse compartment 330 through an opening in the cover 336. The lift arm actuators 344 may thereafter rotate the lift arms 342 to return the empty refuse container 400 to the ground. According to an exemplary embodiment, a door, shown as top door 338, is movably coupled along the cover 336 to seal the opening thereby preventing refuse from escaping the refuse compartment 330 (e.g., due to wind, bumps in the road, etc.).

As shown in FIG. 11, the vehicle 10 includes the ozone cleaning system 100. In one embodiment, the ozone cleaning system 100 is disposed within the cab 316. In such an embodiment, the utility assembly 200 may be (i) integrated directly into the interior of the cab 316 such that the ozone cleaning system 100 does not include the GDU 102 or the GDU 104, and is configured to facilitate decontaminating and neutralizing contaminants disposed within the interior of the cab 316 or (ii) disposed within the utility chamber 160 of the GDU 102 and/or the GDU 104, which may be positioned within the cab 316. In some embodiments, when the ozone cleaning system 100 is disposed within the cab 316, the ozone cleaning system 100 has one or more conduits 108 extending therefrom that extend into the refuse compartment 330 to facilitate decontaminating the interior of the refuse compartment 330. In another embodiment, a second ozone cleaning system 100 is additionally or alternatively disposed within the refuse compartment 330 (e.g., such that the ozone cleaning system 100 within the cab 316 does not require the one or more conduits 108, etc.). In such an embodiment, the utility assembly 200 of the second ozone cleaning system 100 may be integrated directly into the refuse compartment 330 such that the second ozone cleaning system 100 does not include the GDU 102 or the GDU 104. In some embodiments, the second ozone cleaning system 100 disposed in the refuse compartment 330 has one or more conduits 108 extending therefrom that extend into the cab 20 to facilitate decontaminating the interior 22 of the cab 20.

Experimental Testing

Applicant conducted experiments on a decontaminated fabric sample using the ozone cleaning system 100 to identify the efficacy thereof in decontaminating the fabric sample. Specifically, Applicant mailed a fabric sample to St. Louis Testing Laboratories Incorporated ("the Chemists"). The Chemists cut a 2"×2" swatch from the fabric sample and intentionally contaminated it with the chemicals and concentrations shown in Table 1. The Chemists dissolved the chemicals in 2 mL of dichloromethane, and then spread the dichloromethane on the swatch with the chemicals dissolved therein. The Chemists then evaporated the dichloromethane from the contaminated swatch in a 50° C. oven (the chemicals evaporate at a much higher temperature, e.g., greater than 100° C.).

TABLE 1

Mass of Contaminants

| Chemical | Manufacturer | Lot Number | CAS Number | Mass of Contaminant |
| --- | --- | --- | --- | --- |
| Tetrachloroethylene | Sigma-Aldrich | SHBJ7422 | 127-18-4 | 81.0 mg |
| Benzo[a]pyrene | Sigma-Aldrich | SLBV8459 | 50-32-3 | 75.1 mg |
| PCB No 29 | Sigma-Aldrich | SZBF054XV | 15862-07-4 | 22.8 mg |

The Chemists then mailed the contaminated swatch to Applicant. Applicant decontaminated the swatch with the ozone cleaning system 100, and then returned the decontaminated swatch to the Chemists to determine the effectiveness of the decontamination process. The Chemists ultrasonically washed the decontaminated swatch in 30 mL of dichloromethane. The Chemists then evaporated the dichloromethane from the swatch in a 50° C. oven. The Chemists then reconstituted the resulting residue with 5 mL of dichloromethane and injected it into a gas chromatograph-mass spectrometer ("GC-MS"). The GC-MS is able to separate molecules based off of their affinity for the lining of a long column. The separated molecules are then quantified by a mass spectrometer. The parameters of the GC-MS are shown in Table 2.

TABLE 2

GC-MS Parameters

| Gas Chromatograph | Mass Spectrometer | Column | Injection Port Temperature | Oven Temperature Program | Mass Spectrometer Settings |
| --- | --- | --- | --- | --- | --- |
| Agilent 7820A | Agilent 5275 | Zebron ZB-5MS Guardian | 320° C. | 100° C. to 320° C., ramping at 25° C./minute, followed by a 13 minute hold at 320° C. | Specific Ion Monitoring: 166, 252, and 256 AMU |

The Chemists created standards using the same chemicals as the original contaminants introduced onto the swatch. The standards and the swatch extract were then analyzed by GC-MS, and a concentration of the residual chemicals was calculated, as shown in Table 3.

TABLE 3

Analysis of Swatch Contaminants

| Chemical | Concentrate in Extract (PPM w/v) | Mass of Extracted Material (mg) | Percent of Original Contaminant Recovered |
| --- | --- | --- | --- |
| Tetrachloroethylene | <20 | <0.1 | <0.1% |
| Benzo[a]pyrene | 415 | 2.075 | 3% |
| PCB No 29 | 1031 | 5.155 | 23% |

From the testing, the Chemists determined that the decontamination process implemented by the ozone cleaning system 100 removed 99.9% of the tetrachloroethylene, 97% of the benzo[a]pyrene, and 77% of the polychlorinated biphenyl No 29 ("PCB No 29") from the swatch.

As utilized herein, the terms "approximately", "about", "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like, as used herein, mean the joining of two members directly or indirectly to one another. Such joining may be stationary (e.g., permanent) or movable (e.g., removable, releasable, etc.). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the figures. It should be noted that the orientation of various elements may differ according to other exemplary embodiments, and that such variations are intended to be encompassed by the present disclosure.

Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is otherwise understood with the context as used in general to convey that an item, term, etc. may be either X, Y, Z, X and Y, X and Z, Y and Z, or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

It is important to note that the construction and arrangement of the elements of the systems and methods as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. It should be noted that the elements and/or assemblies of the components described herein may be constructed from any of a wide variety of materials that provide sufficient strength or durability, in any of a wide variety of colors, textures, and combinations. Accordingly, all such modifications are intended to be included within the scope of the present inventions. Other substitutions, modifications, changes, and omissions may be made in the design, operating conditions, and arrangement of the preferred and other exemplary embodiments without departing from scope of the present disclosure or from the spirit of the appended claims.

The invention claimed is:

1. An ozone cleaning system comprising:
    a housing defining an interior chamber, the housing including a dividing wall separating the interior chamber into (i) a first chamber configured to selectively receive contaminated equipment and (ii) a second chamber coupled to the first chamber;
    an ozone generator configured to generate ozone;
    a humidifying unit configured to generate water vapor, wherein the ozone generator and the humidifying unit provide the ozone and the water vapor to the first chamber such that moist, ozonated, clean air is circulated throughout the first chamber to interact with the contaminated equipment to generate moist, ozonated, contaminated air during a decontamination process of the contaminated gear;
    a filter positioned along the dividing wall;
    a catalyst, wherein the filter and the catalyst are configured to neutralize residual ozone and contaminants within the moist, ozonated, contaminated air; and
    a blower configured to provide the moist, ozonated, contaminated air from the first chamber, through the filter and the catalyst, and out of the second chamber to an exterior environment that surrounds the housing following the decontamination process of the contaminated equipment.

2. The ozone cleaning system of claim 1, wherein the filter is a photocatalytic oxidation filter that includes the catalyst and a light source.

3. The ozone cleaning system of claim 2, wherein the light source is an ultraviolet light source.

4. The ozone cleaning system of claim 1, wherein the catalyst is a titanium dioxide catalyst.

5. The ozone cleaning system of claim 3, wherein the ultraviolet light source provides ultraviolet light having a wavelength spectrum between 250 nanometers and 415 nanometers.

6. The ozone cleaning system of claim 1, wherein the first chamber includes at least one divider that subdivides the first chamber into a plurality of zones.

7. The ozone cleaning system of claim 6, wherein the at least one divider is at least partially permeable.

8. The ozone cleaning system of claim 6, wherein at least one of (i) the ozone generator is configured to facilitate providing the ozone to each of the plurality of zones individually or (ii) the humidifying unit is configured to facilitate providing the water vapor to each of the plurality of zones individually.

9. The ozone cleaning system of claim 1, wherein the ozone cleaning system is a standalone unit.

10. The ozone cleaning system of claim 1, wherein the ozone cleaning system is integrated into a compartment of a vehicle.

11. The ozone cleaning system of claim 1, wherein the first chamber is a cab of a vehicle.

12. The ozone cleaning system of claim 1, wherein the first chamber is a refuse compartment of a vehicle.

* * * * *